United States Patent [19]

Patel

[11] Patent Number: 5,395,389
[45] Date of Patent: Mar. 7, 1995

[54] METHOD FOR REMOVING AND REPLACING A CORONARY BALLOON CATHETER DURING CORONARY ANGIOPLASTY

[76] Inventor: Piyush V. Patel, 3401 Salisbury Pl., Midland, Tex. 79707

[21] Appl. No.: 118,092

[22] Filed: Sep. 8, 1993

Related U.S. Application Data

[63] Continuation of Ser. No. 828,560, Jan. 31, 1992, abandoned.

[51] Int. Cl.6 .............................................. A61M 29/02
[52] U.S. Cl. ....................................... 606/194; 604/96
[58] Field of Search .................. 606/194, 192; 604/96, 604/101

[56] References Cited

U.S. PATENT DOCUMENTS

| | | |
|---|---|---|
| 4,748,984 | 6/1988 | Patel . |
| 4,755,176 | 7/1988 | Patel . |
| 4,781,682 | 11/1988 | Patel . |
| 4,784,639 | 11/1988 | Patel . |
| 4,832,028 | 5/1989 | Patel . |
| 4,932,959 | 6/1990 | Horzewski et al. ............... 604/96 X |
| 5,000,743 | 3/1991 | Patel . |
| 5,102,390 | 4/1992 | Crittenden et al. .................. 604/194 |

*Primary Examiner*—Michael H. Thaler
*Attorney, Agent, or Firm*—Herbert J. Hammond

[57] ABSTRACT

An apparatus for removing and replacing a coronary balloon catheter during coronary angioplasty comprises a double catheter. A guiding catheter is inserted into the opening of a coronary artery. An auxiliary balloon catheter is disposed axially inside the guiding catheter, and is secured along the side wall of the guiding catheter. A balloon is secured near the distal end of the auxiliary balloon catheter.

A method for removing and replacing a coronary balloon catheter during coronary angioplasty comprises the steps of inserting a guiding catheter containing an auxiliary balloon catheter in the opening of a coronary artery; inserting a first coronary balloon catheter through the guiding catheter into the coronary artery; withdrawing the first coronary balloon catheter from the coronary artery into the guiding catheter until the first coronary balloon catheter is proximal to the balloon on the auxiliary balloon catheter; inflating the balloon on the auxiliary balloon catheter; removing the first coronary balloon catheter; and inserting a second coronary balloon catheter through the guiding catheter into the coronary artery.

4 Claims, 3 Drawing Sheets

METHOD FOR REMOVING AND REPLACING A CORONARY BALLOON CATHETER DURING CORONARY ANGIOPLASTY

This is a continuation of application Ser. No. 07/828,560, filed Jan. 31, 1991, now abandoned.

TECHNICAL FIELD

This invention relates generally to the field of medical equipment and, more particularly to an apparatus and method for removing and replacing a coronary balloon catheter during coronary angioplasty.

BACKGROUND OF THE INVENTION

Physicians perform coronary angioplasty when a coronary artery has become partially blocked by a stenotic lesion. A stenotic lesion is an abnormal narrowing of an artery due to injury or disease.

The angioplasty procedure involves the introduction of a catheter system into the artery, by way of the femoral artery, under local anesthesia. The catheter system includes a guiding catheter and a dilating catheter. The end of the guiding catheter is inserted into the opening of the coronary artery.

The dilating catheter is passed through the guiding catheter into the coronary artery. The tip of the dilating catheter is passed through the stenotic lesion in the coronary artery. A balloon on the tip of the dilating catheter is then inflated with a fluid. The balloon forces the blockage open and enlarges the lumen, or passage, through the artery.

Sometimes during coronary angioplasty, the physician determines that he must replace the dilating catheter. The physician may have discovered that the existing balloon is too small or too large to force the blockage open.

Prior art methods use a conventional guiding catheter known in the art. The primary function of the guiding catheter is to assist in insertion of the dilating catheter into the coronary artery.

There are two lengths of guidewires generally available for use in coronary angioplasties: long guidewires and standard (short) guidewires. Prior art procedures require the use of a long guidewire to change balloons because there is no mechanism on prior art guiding catheters to maintain the position of the guidewire in the guiding catheter. Thus, when the dilating catheter is withdrawn from the guiding catheter, the dilating catheter pulls the guidewire out with it. Before a new dilating catheter can be inserted, the physician must reinsert the first guidewire or a replacement guidewire.

In addition, prior art procedures sometimes require replacing the existing balloon with a balloon having less flexibility. Replacing the balloon using prior art techniques uses additional time, exposing the patient to additional risks associated with prolonged anesthesia. Finally, prior art guiding catheters have no feature for maintaining the position of the guidewire in the guiding catheter if a dilating catheter must be removed.

SUMMARY OF THE INVENTION

The present invention comprises a highly practical apparatus and method for removing and replacing a coronary balloon catheter during coronary angioplasty which overcome the foregoing disadvantages associated with the prior art.

An apparatus for removing and replacing a coronary balloon catheter during coronary angioplasty comprises a double catheter. A conventional aortic guiding catheter is dimensioned to be inserted into the opening of a coronary artery. A smaller diameter auxiliary balloon catheter is disposed axially within the guiding catheter. The auxiliary balloon catheter is secured to the interior wall of the guiding catheter. An inflatable balloon is located near the distal end of the auxiliary balloon catheter. A port located on the proximal end of the auxiliary balloon catheter outside the guiding catheter receives fluids for injection into the balloon. The apparatus may include an opening in the side wall of the guiding catheter for preventing a vacuum from being created as the coronary balloon catheter is withdrawn from the guiding catheter.

A method for removing and replacing a coronary balloon catheter during coronary angioplasty using the apparatus of the invention includes the steps of inserting a guiding catheter containing an auxiliary balloon catheter into the opening of a coronary artery; inserting a guidewire through the guiding catheter; positioning the guidewire in the coronary artery across the lesion to be removed; threading a first coronary balloon catheter on the guidewire into the coronary artery; withdrawing the first coronary balloon catheter from the coronary artery into the guiding catheter until the distal end of the first coronary balloon catheter is proximal to the balloon on the auxiliary balloon catheter; inflating the balloon on the auxiliary balloon catheter; removing the first coronary balloon catheter; and threading a second coronary balloon catheter on the guidewire into the coronary artery.

DESCRIPTION OF THE DRAWINGS

For a more complete understanding of the present invention and the advantages thereof, reference is now made to the following Detailed Description taken in conjunction with the accompanying Drawings in which.

DETAILED DESCRIPTION

Figure 1:
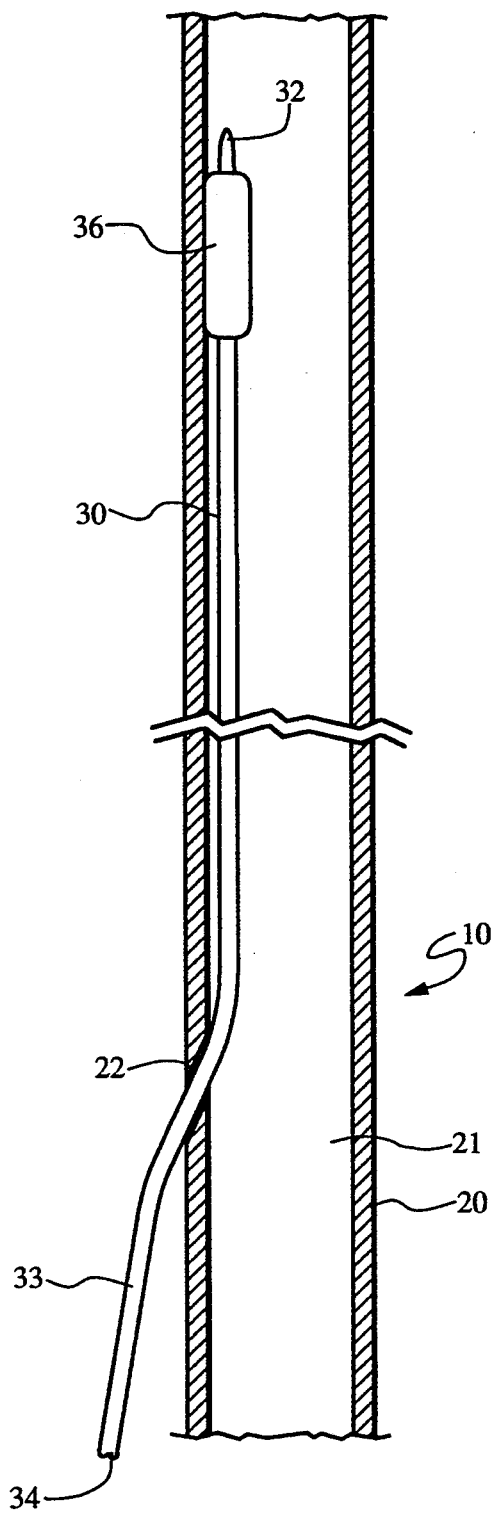
FIG. 1 is a cross-sectional view of the double catheter of the present invention.

Referring now to the Drawings, wherein like reference characters designate like or similar parts throughout the six views, FIG. 1 is a cross-sectional view of the double catheter 10 according to the present invention.

The double catheter 10 comprises a guiding catheter 20 and a substantially smaller diameter auxiliary balloon catheter 30 disposed axially therein. Guiding catheter 20 is a conventional aortic catheter of the type commonly used in coronary angioplasty.

An auxiliary balloon catheter 30 has a closed, distal end 32, a balloon 36 located near the distal end 32 thereof, and a proximal end 33 containing a port 34. The distal end 32 and balloon 36 of catheter 30 are located inside the lumen 21 of guiding catheter 20. The proximal end 33 is disposed outside of the guiding catheter 20 through an opening 22 in the wall thereof. Balloon 36 of catheter 30 is affixed to the lumen wall of the guiding catheter 20 so that movement of catheter 30 in guiding catheter 20 is restrained.

Fluid may be injected through port 34 to inflate balloon 36 as needed. When inflated, balloon 36 completely obstructs the inside lumen 21 of the guiding catheter 20. When the fluid is withdrawn through port 34, balloon 36 will deflate, but will remain affixed to the inside wall of guiding catheter 20.

The double catheter 10 of the present invention may be used to quickly and easily remove and replace coronary balloon catheters during coronary angioplasty. At the beginning of the procedure, the physician selects a coronary balloon catheter of predetermined size and positions the coronary balloon catheter in the coronary artery via guiding catheter 20. During the procedure, however, the physician may need to replace the balloon for any of several reasons—the balloon may be too large or too small to force the blockage from the coronary artery, it may be insufficiently flexible for the procedure, or it may have some other defect requiring replacement.

Figure 2:
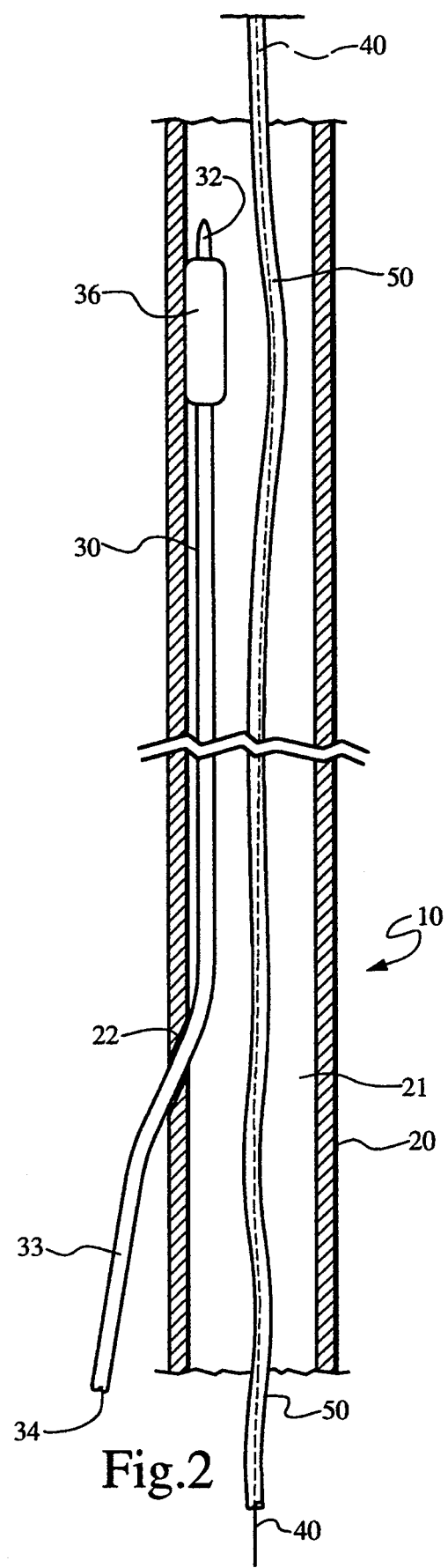
FIG. 2 is a cross-sectional view of the double catheter of the present invention during coronary angioplasty before balloon replacement, before the balloon on the auxiliary balloon .catheter has been inflated.
Figure 3:
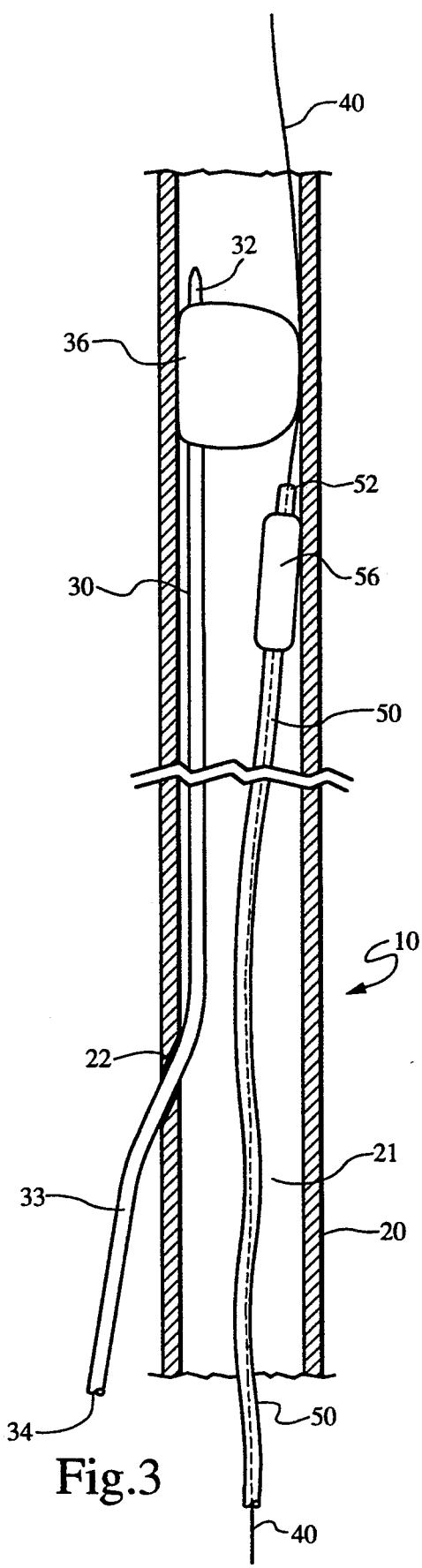
FIG. 3 is a cross-sectional view of the double catheter of the present invention during coronary angioplasty before balloon replacement, after the balloon on the auxiliary balloon catheter has been inflated.

FIGS. 2 and 3 show double catheter 10 of the present invention during various stages of a coronary angioplasty involving balloon replacement. The guiding catheter 20 has been inserted and positioned in the osteum of the coronary artery, and a small guidewire 40 has been inserted into guiding catheter 20. The guidewire 40 is then guided through catheter 20 into the coronary artery where it is placed through the lesion to be removed.

A coronary balloon catheter 50 is threaded over guidewire 40 to perform the balloon angioplasty. Coronary balloon catheter 50 has a balloon 52 positioned near its distal end.

FIG. 2 shows double catheter 10 of the present invention during coronary angioplasty before coronary balloon catheter 50 is replaced. The balloon 36 on catheter 30 is not inflated. Guidewire 40 extends axially in guiding catheter 20 past the lesion in the coronary artery (not shown). The coronary balloon catheter 50 encloses guidewire 40, and the balloon (not shown) on catheter 50 is positioned across the lesion in the coronary artery. At this stage, the physician may decide to replace balloon 52 by withdrawing balloon catheter 50.

Guiding catheter 20 and guidewire 40 are left in place. The coronary balloon catheter 50 is withdrawn from the coronary artery into guiding catheter 20 until the distal end of catheter 50 is proximal to balloon 36 of auxiliary balloon catheter 30. Fluid is then injected into balloon catheter 30 via port 34 to inflate balloon 36.

FIG. 3 shows double catheter 10 of the present invention during coronary angioplasty after balloon 36 of auxiliary balloon catheter 30 has been inflated. The inflated balloon 36 completely obstructs the lumen 21 of guiding catheter 20, pressing guidewire 40 against the side wall thereof, preventing movement of guidewire 40 while the coronary balloon catheter 50 is withdrawn from guiding catheter 20.

The physician selects a new coronary balloon catheter 50'. The replacement coronary balloon catheter 50' is then threaded on guidewire 40 into guiding catheter 20. Fluid is withdrawn from auxiliary balloon catheter 30 via port 34, causing balloon 36 to deflate and provide clearance for balloon 56' to pass through the distal end of guiding catheter 20.

Figure 4:
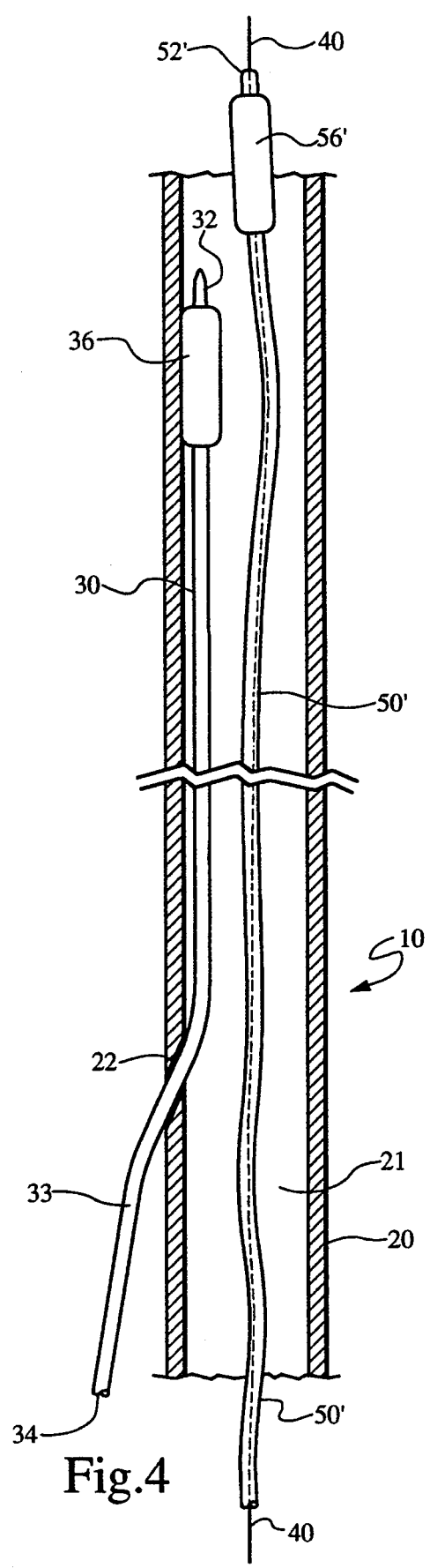
FIG. 4 is a cross-sectional view of the double catheter of the present invention during coronary angioplasty following balloon replacement, after the balloon on the auxiliary balloon catheter has been deflated.

FIG. 4 shows a cross-sectional view of double catheter 10 of the present invention during coronary angioplasty following balloon replacement. The auxiliary balloon catheter 30 is located inside of guiding catheter 20, with the balloon 36 deflated. Guidewire 40 extends through guiding catheter 20 into the coronary artery, having been restrained from movement by balloon 36. Replacement coronary balloon catheter 50', with deflated balloon 56' near its distal end 52' is threaded on guidewire 40 and will be advanced into the coronary artery and repositioned across the lesion to be removed. The physician will then continue with the procedure, inflating balloon 56' as required.

Removing and replacing a coronary balloon catheter during coronary angioplasty using the double catheter and method of the present invention does not require a long guidewire or an extension added to the standard (short) guidewire. Because the inflated balloon 36 holds the guidewire 40 in place inside the guiding catheter 20, replacement of a coronary balloon catheter takes less time than with prior art apparatus and procedures.

Figures 5, 6:
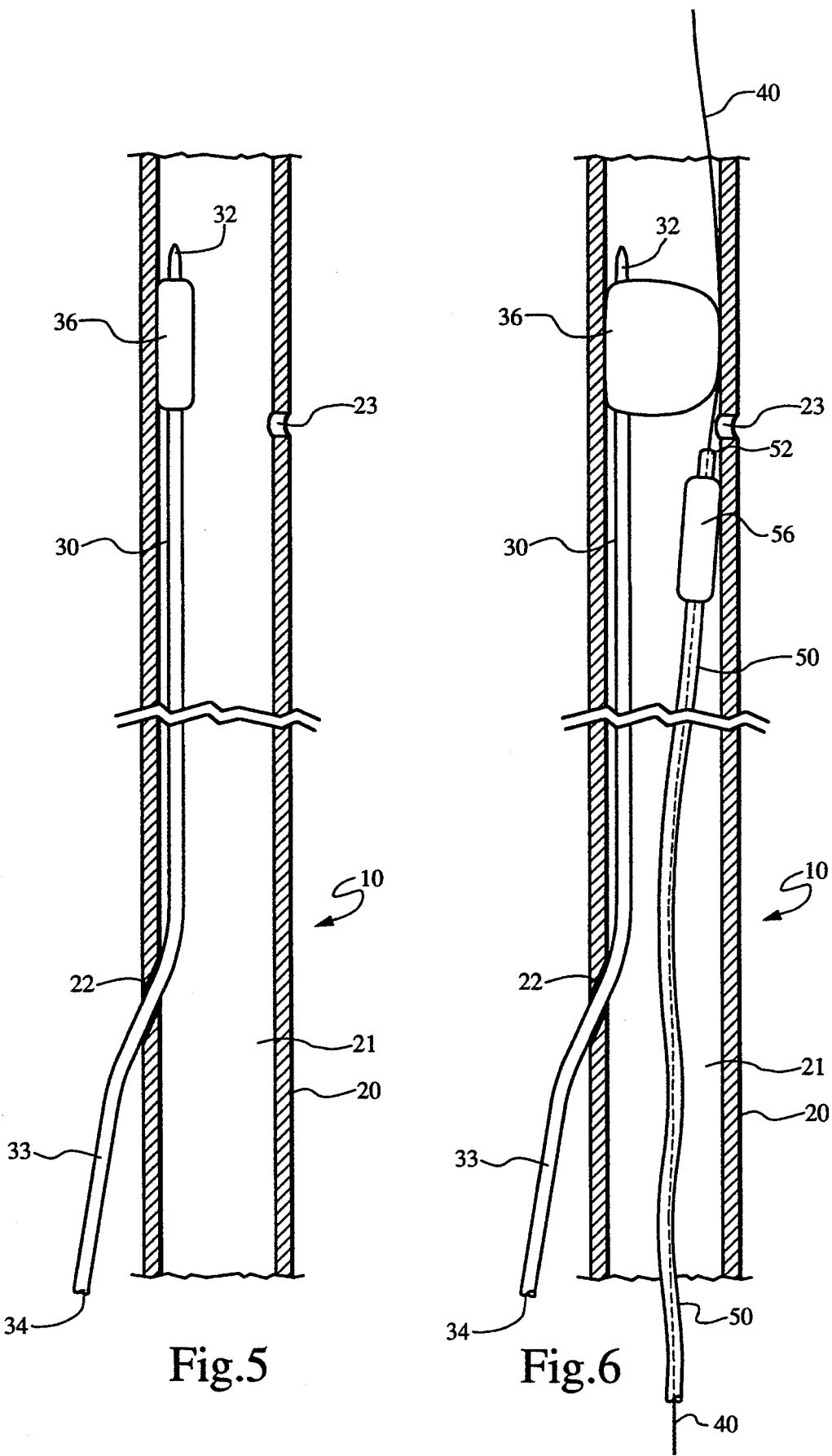
FIG. 5 is a cross-sectional view of an alternative embodiment of the double catheter of the present invention, illustrating the opening in the side wall of the guiding catheter.
FIG. 6 is a cross-sectional view of the alternative embodiment of the double catheter during coronary angioplasty before balloon replacement, after the balloon on the auxiliary balloon catheter has been inflated.

FIG. 5 shows a cross-sectional view of an alternative embodiment of the double catheter of the present invention. There is an opening 23 in the side wall of the guiding catheter. Opening 23 is proximal to balloon 36 on auxiliary balloon catheter 30.

When the first coronary balloon catheter 50 is withdrawn from guiding catheter 20, the withdrawal may cause a negative vacuum inside guiding catheter 20. The negative vacuum causes atmospheric air to rush into guiding catheter 20, filling the space previously occupied by coronary balloon catheter 50. Air entering guiding catheter 20 in this manner may create an air embolism which is potentially life-threatening to the patient.

Opening 23 prevents a negative vacuum in guiding catheter 20 during withdrawal of catheter 50. Opening 23 allows blood, rather than air, to flow into guiding catheter 20.

FIG. 6 shows a cross-sectional view of the alternative embodiment of the double catheter during coronary angioplasty before balloon replacement, after balloon 36 on auxiliary balloon catheter 30 has been inflated.

As coronary balloon catheter 50 is withdrawn from guiding catheter 20, blood enters catheter 20 through opening 23, filling the space previously occupied by catheter 50. No vacuum is created in guiding catheter 20 as catheter 50 is withdrawn.

Although preferred and alternative embodiments of the present invention have been illustrated in the accompanying Drawings and described in the foregoing Detailed Description, it will be understood that the invention is not limited to the embodiments disclosed, but is capable of numerous rearrangements, modifications and substitutions of parts and elements without departing from the spirit of the invention.

I claim:

1. A method for removing and replacing a coronary balloon catheter during coronary angioplasty, comprising the steps of:
   inserting a guiding catheter containing an auxiliary balloon catheter having a balloon near the distal end thereof into the opening of a coronary artery;
   inserting a guidewire through the guiding catheter into the coronary artery;
   advancing a first coronary balloon catheter along the guidewire in the guiding catheter into the coronary artery;
   withdrawing the first coronary balloon catheter from the coronary artery along the guidewire through the guiding catheter;
   inflating the balloon on the auxiliary balloon catheter to restrain movement of the guidewire in the guiding catheter as the first coronary balloon catheter is withdrawn from the guiding catheter;
   withdrawing the first coronary balloon catheter from the guiding catheter; and
   advancing a second coronary balloon catheter along the guidewire in the guiding catheter.

2. The method for removing and replacing a coronary balloon catheter during coronary angioplasty of claim 1 further comprising the step of withdrawing fluid from the auxiliary balloon catheter to deflate the balloon on the auxiliary balloon catheter to provide clearance for the second coronary balloon catheter to advance into the opening of the coronary artery.

3. The method for removing and replacing a coronary balloon catheter during coronary angioplasty of claim 1 wherein the step of inflating the balloon on the auxiliary balloon catheter secured inside the guiding catheter includes injecting fluid into the port of the auxiliary balloon catheter.

4. A method for removing and replacing a coronary balloon catheter during coronary angioplasty, comprising the steps of:
   inserting a guiding catheter containing an auxiliary balloon catheter having a balloon near the distal end and a port at the proximal end thereof into the opening of a coronary artery;
   inserting a guidewire through the guiding catheter into the coronary artery;
   advancing a first coronary balloon catheter along the guidewire through the guiding catheter into the coronary artery;
   withdrawing the first coronary balloon catheter from the coronary artery along the guidewire into the guiding catheter until the distal end of the first coronary balloon catheter is proximal to the balloon on the auxiliary balloon catheter;
   injecting fluid through the port of the auxiliary balloon catheter to inflate the balloon on said auxiliary balloon catheter;
   withdrawing the first coronary balloon catheter completely from the guiding catheter;
   advancing a second coronary balloon catheter along the guidewire through the guiding catheter until the distal end of the second coronary balloon catheter is proximal to the balloon on the auxiliary balloon catheter;
   withdrawing fluid through the port of the auxiliary balloon catheter to deflate the balloon on said auxiliary catheter to provide clearance for the second coronary balloon catheter to advance into the opening of the coronary artery; and
   further advancing the second coronary balloon catheter into the coronary artery.

* * * * *